(12) United States Patent
Ashworth (10) Patent No.: US 9,601,007 B2
(45) Date of Patent: Mar. 21, 2017

(54) SELF-PROPELLED FLOOR APPARATUS AND SYSTEM HAVING A BACTERICIDAL FUNCTION

(71) Applicants: FLOORBOTICS INC., Rollingwood, TX (US); METAPO INC., San Jose, CA (US)

(72) Inventor: Guy Thomas Duncan Ashworth, Rollingwood, TX (US)

(73) Assignees: FLOORBOTICS INC., Rollingwood, TX (US); METAPO INC., San Jose, CA (US)

( * ) Notice: Subject to any disclaimer, the term of this patent is extended or adjusted under 35 U.S.C. 154(b) by 0 days.

(21) Appl. No.: 15/008,299

(22) Filed: Jan. 27, 2016

(65) Prior Publication Data

US 2016/0221195 A1    Aug. 4, 2016

Related U.S. Application Data

(60) Provisional application No. 62/109,593, filed on Jan. 29, 2015.

(51) Int. Cl.
| | |
|---|---|
| *A61L 2/08* | (2006.01) |
| *G08C 17/02* | (2006.01) |
| *B25J 5/00* | (2006.01) |
| *B25J 9/16* | (2006.01) |
| *A61L 2/10* | (2006.01) |
| *A61L 2/24* | (2006.01) |

(52) U.S. Cl.
CPC ............... *G08C 17/02* (2013.01); *A61L 2/10* (2013.01); *A61L 2/24* (2013.01); *B25J 5/00* (2013.01); *B25J 9/1666* (2013.01); *Y10S 901/01* (2013.01)

(58) Field of Classification Search
USPC ... 250/453.11, 454.11, 455.11, 492.1, 493.1, 250/504 R, 504 H
See application file for complete search history.

(56) References Cited

U.S. PATENT DOCUMENTS

| 5,321,614 A | 6/1994 | Ashworth |
| 8,779,391 B2 | 7/2014 | Flaherty et al. |
| 2005/0022330 A1* | 2/2005 | Park ...................... A47L 7/0061 15/319 |
| 2012/0223216 A1* | 9/2012 | Flaherty .................... A61L 2/10 250/214.1 |

(Continued)

*Primary Examiner* — Nicole Ippolito
(74) *Attorney, Agent, or Firm* — Muncy, Geissler, Olds & Lowe, P.C.

(57) ABSTRACT

A self-propelled apparatus includes: a self-propelled platform having a recessed chamber located in the bottom side, a control unit mounted in the self-propelled platform for controlling the moving path of the self-propelled platform in a predominantly grid-pattern that causes the self-propelled platform to mainly move in predominantly straight lines, a battery, one or multiple germicidal ultraviolet lights exhibiting an elongated shape and mounted in the self-propelled platform within the recessed chamber in such a manner that the longitudinal axis of the germicidal ultraviolet lights is kept in parallel to the linear moving direction of the self-propelled platform, and obstacle sensors. The self-propelled apparatus utilizes a wireless module for wireless communication with an external smart device that has built therein an application software for controlling and displaying the operating status of the self-propelled apparatus.

19 Claims, 8 Drawing Sheets

(56) References Cited

U.S. PATENT DOCUMENTS

2014/0330452 A1* 11/2014 Stewart ................ B25J 11/0085
                                                              701/2
2016/0151530 A1*  6/2016 Kawanabe .............. H01T 23/00
                                                            422/124

* cited by examiner

SELF-PROPELLED FLOOR APPARATUS AND SYSTEM HAVING A BACTERICIDAL FUNCTION

BACKGROUND OF THE INVENTION

1. Field of the Invention

The present invention relates to self-propelled robot technology and more particularly, to a self-propelled apparatus and system having a bactericidal function.

2. Description of the Related Art

Pathogens are often found on floor surfaces such as bathrooms, day care centers, hospitals, doctors' waiting rooms, gymnasiums, schools, homes, and the like. UV light is a proven form of chemical-free sterilization. The integration of germicidal lamps with robotic control algorithms and hardware provides a low-labor-cost and chemical-free supplement to traditional cleaning methods.

Infectious diseases are routinely reported. Announcements include *E-coli,* MRSA, tuberculosis, Legionnaires disease, staphylococcus, streptococcus, pneumonia, bronchitis, giardia, and many others.

Commercially-available robotic home robots may address the vacuum and mopping aspects of cleaning but not the disinfecting needs. A simple-to-use, chemical-free alternative is needed. One that has a long run time, requires no training by the owner, and effectively kills pathogens on the floor while covering an adequate amount of floor space.

Techniques for combining a self-propelled apparatus with a germicidal ultraviolet light are known. For example, U.S. Pat. No. 8,779,391 describes the arrangement of a germicidal ultraviolet light in a self-propelled system so that the system is capable of "seek and destroy" functionality by navigating towards contaminated areas and irradiating those areas with ultraviolet light accordingly. However, this technique does not consider the relationship between the moving path of the self-propelled platform and the germicidal ultraviolet light, and thus, there is a room for improvement of in sterilization performance—specifically, applying an adequate dose of UV light to be effective in eradicating pathogens.

U.S. Pat. No. 5,321,614, issued to the present inventor, discloses a navigational apparatus and method for guiding an autonomous vehicle throughout a work area. However, this patent does not describe the combination of the navigational apparatus with a germicidal ultraviolet light

SUMMARY OF THE INVENTION

The present invention is hereby described with these needs in mind. It is the main object of the present invention to provide a self-propelled apparatus having a bactericidal function, which achieves better germicidal effect than the prior art patents when sterilizing the floor.

To achieve this and other objectives of the present invention, a self-propelled apparatus comprises a self-propelled platform having a recessed chamber located in a bottom side thereof, a control unit mounted in the self-propelled platform and adapted for controlling the moving path of the self-propelled platform in a predominantly grid-pattern that causes the self-propelled platform to mainly move in straight lines, a battery electrically coupled to the control unit to provide the necessary working electric energy, at least one germicidal ultraviolet light exhibiting an elongated shape and mounted in the self-propelled platform within the recessed chamber in such a manner that the longitudinal axis of the at least one germicidal ultraviolet light is kept in parallel to the linear moving direction of the self-propelled platform, the at least one germicidal ultraviolet light being electrically coupled to the control unit and controllable by the control unit to radiate light, and a plurality of obstacle sensors mounted in the self-propelled platform and electrically coupled to the control unit and adapted for detecting the presence of obstacles for enabling the control unit to modify the traveling of the self-propelled platform on inputs from the obstacle sensors.

As the longitudinal axis of the germicidal ultraviolet light exhibits a parallel relationship with the moving direction of the self-propelled platform and the self-propelled platform is mainly controlled to move in straight lines according to the predetermined grid-pattern, an intense UV dose can be applied by the germicidal ultraviolet lights to the floor so as to achieve optimal bactericidal effects.

It is another object of the present invention to provide a self-propelled system having a bactericidal function, which achieves better bactericidal effects than prior art patents, and allows the user to use a smart device for displaying and controlling the operation mode and state of the self-propelled platform when sterilizing the floor.

To achieve this and other objects of the present invention, a self-propelled system comprises a self-propelled platform having a recessed chamber located in a bottom side thereof, a control unit mounted in the self-propelled platform and adapted for controlling the moving path of the self-propelled platform in a predominantly grid-pattern that causes the self-propelled platform to mainly move in straight lines, a battery electrically coupled to the control unit to provide the necessary working electric energy, at least one germicidal ultraviolet light exhibiting an elongated shape and mounted in the self-propelled platform within the recessed chamber in such a manner that the longitudinal axis of the at least one germicidal ultraviolet light is kept in parallel to the linear moving direction of the self-propelled platform, the at least one germicidal ultraviolet light being electrically coupled to the control unit and controllable by the control unit to radiate light, a plurality of obstacle sensors mounted in the self-propelled platform and electrically coupled to the control unit and adapted for detecting the presence of obstacles for enabling the control unit to modify the traveling of the self-propelled platform on the basis of the inputs from the obstacle sensors, a wireless module mounted in the self-propelled platform and electrically coupled to the control unit for communication with a smart device in a wireless manner, and an application software installed in the smart device for execution by the smart device. The self-propelled platform utilizes the wireless module to wirelessly communicate with the smart device and transmitting data. However, the self-propelled platform is completely capable of operating autonomously without a smart device. The smart device executes the application software to interpret the data and displays the data in a way that a general user is able to understand, and also utilizes the wireless communication relationship between the smart device and the wireless module to transmit instructions to the control unit.

Thus, when sterilizing the floor, the self-propelled system achieves better bactericidal effects than prior art patents, and allows the user to use a smart device for optionally displaying and controlling the operation mode and state of the self-propelled platform.

Other advantages and features of the present invention will be fully understood by reference to the following specification in conjunction with the accompanying drawings, in which like reference signs denote like components of structure.

DETAILED DESCRIPTION OF THE INVENTION

Referring to FIGS. 1-5, a self-propelled apparatus 10 having a bactericidal function in accordance with the present invention is shown. The self-propelled apparatus 10 comprises a self-propelled platform 11, a control unit 21, a battery 31, at least one germicidal ultraviolet light 41 and a plurality of obstacle sensors 51.

The self-propelled platform 11 has a recessed chamber 12 located in a bottom side thereof.

The control unit 21 is mounted in the self-propelled platform 11, and adapted for controlling the moving path of the self-propelled platform 11 in a predominantly grid-pattern that causes self-propelled platform 11 to mainly move in straight lines thus maximizing the amount of floor coverage.

The battery 31 is electrically coupled to the control unit 21 to provide the necessary working electric energy.

The at least one germicidal ultraviolet light 41 exhibits an elongated shape, and is mounted in the self-propelled platform 11 within the recessed chamber 12 with the longitudinal axis thereof kept in parallel to the linear moving direction of the self-propelled platform 11. Further, the at least one germicidal ultraviolet light 41 is electrically coupled to the control unit 21 and controllable by the control unit 21 to radiate light. The number of the at least one germicidal ultraviolet lights 41 can be 1, 2, or more than 2. In this embodiment, two germicidal ultraviolet lights 41 are provided and arranged in parallel. Further, each germicidal ultraviolet light 41 can he formed of an elongated UV lamp or PL type UV lamp, or an elongated lamp consisting of multiple UV light-emitting diodes. In this embodiment, PL type UV lamp is used.

The multiple obstacle sensors 51 are mounted in the self-propelled platform 11 and electrically coupled to the control unit 21, and adapted to detect the presence of protruded obstacles (such as wall, furniture) or recessed obstacles (such as stairs), enabling the control unit 21 to modify the traveling of the self-propelled platform 11 on the basis of the positions of the obstacles.

In this first embodiment, the depth of the recessed chamber 12 is larger than the thickness of the at least one germicidal ultraviolet light 41 so that the two germicidal ultraviolet lights 41 can be completely accommodated in the recessed chamber 12 without protruding over the bottom surface of the self-propelled platform 11. This design ensures that the two germicidal ultraviolet lights 41 will not be hit and damaged by an external object as the self-propelled platform 11 is traveling. Further, in this first embodiment, the mounting position of the two germicidal ultraviolet lights 41 can be so designed such that when the self-propelled platform 11 is placed on the floor, the center of the germicidal ultraviolet lights 41 is kept at a distance of approximately 2.5 cm above the floor surface, enabling the germicidal ultraviolet lights 41 to apply an intense UV dose to the floor so as to achieve optimal bactericidal effects. Further, two lamp holders 14 are mounted in the recessed chamber 12 of the self-propelled platform 11 so that the two germicidal ultraviolet lights 41 can be respectively and detachably mounted in the lamp holders 14, facilitating replacement.

After understanding of the structural details of the self-propelled apparatus 10 in accordance with the first embodiment of the present invention, the operation of the self-propelled apparatus 10 is outlined hereinafter.

Figure 1:
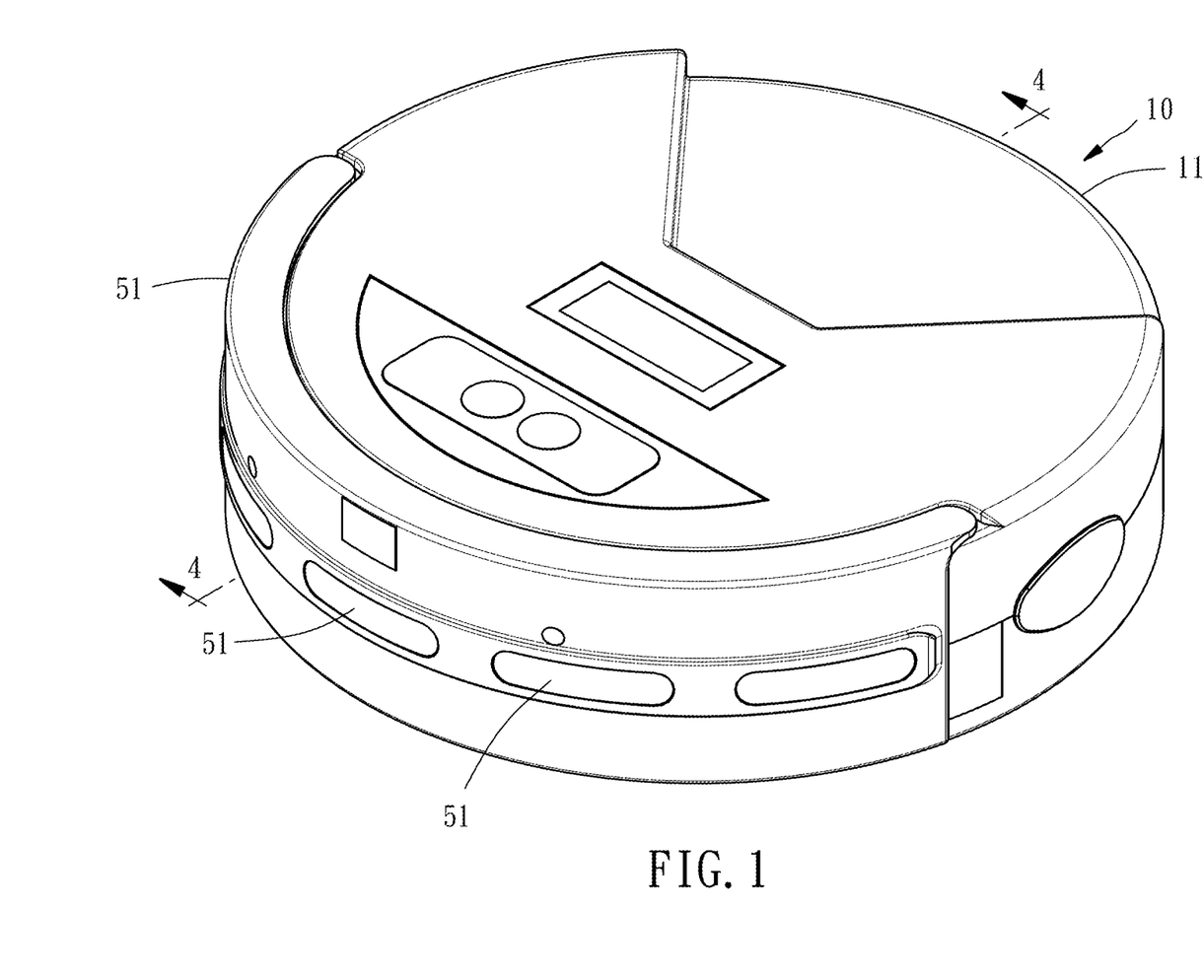
FIG. 1 is an oblique top elevational view of a self-propelled apparatus in accordance with a first embodiment of the present invention.
Figure 2:
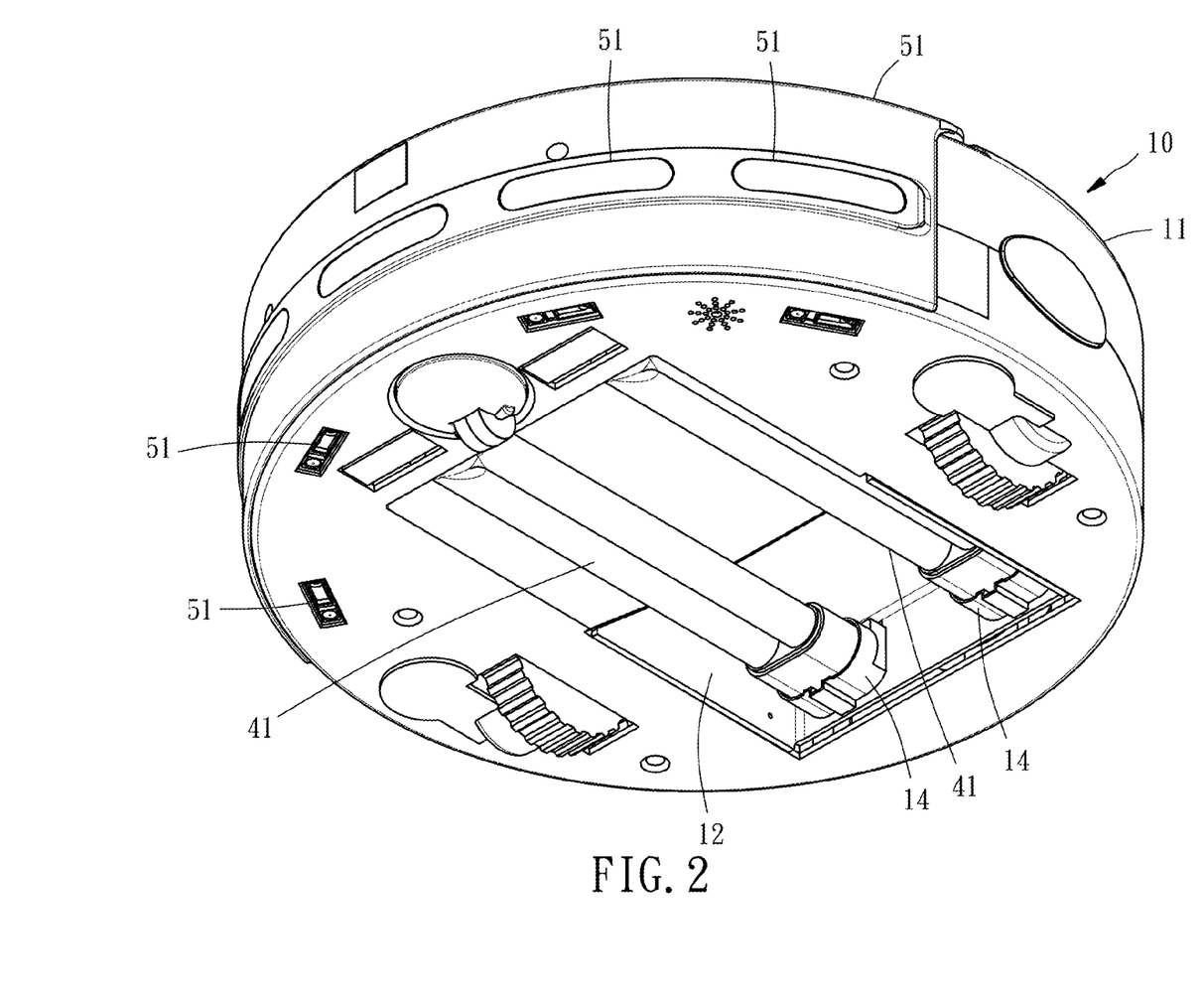
FIG. 2 is an oblique bottom elevational view of the self-propelled apparatus in accordance with the first embodiment of the present invention.
Figure 3:
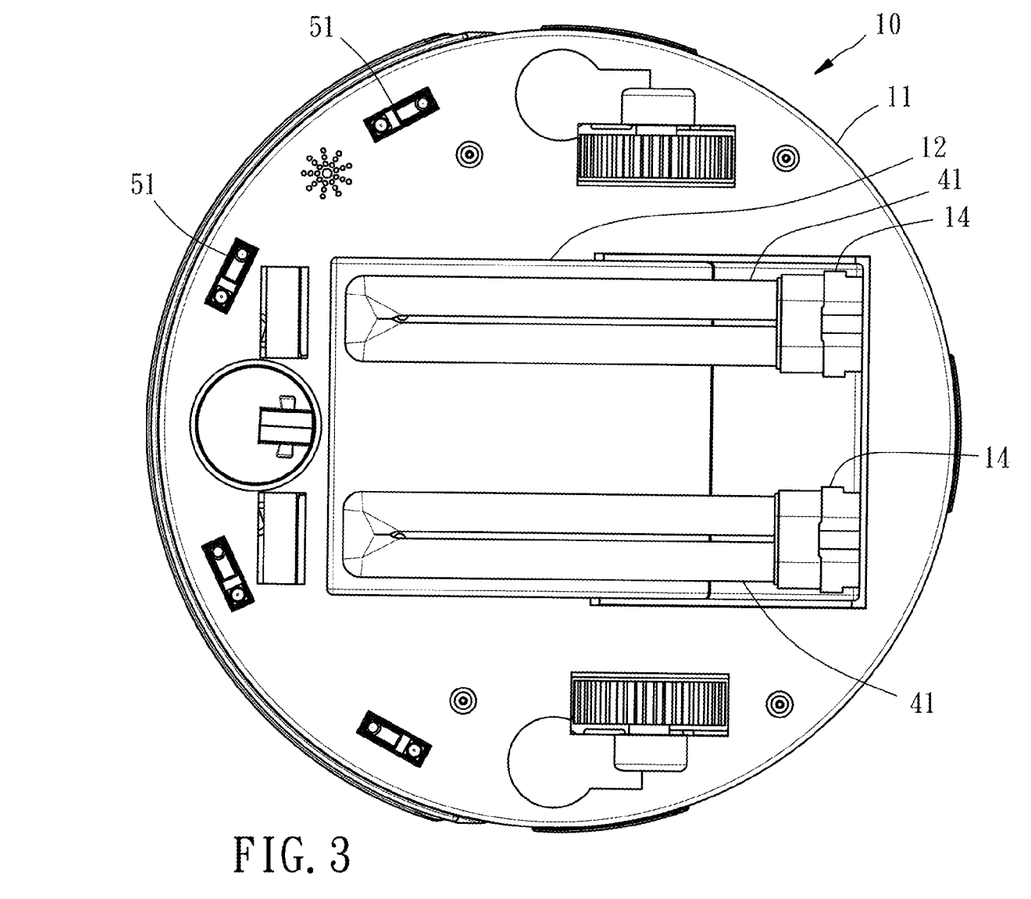
FIG. 3 is a bottom view of the self-propelled apparatus in accordance with the first embodiment of the present invention.
Figure 4:
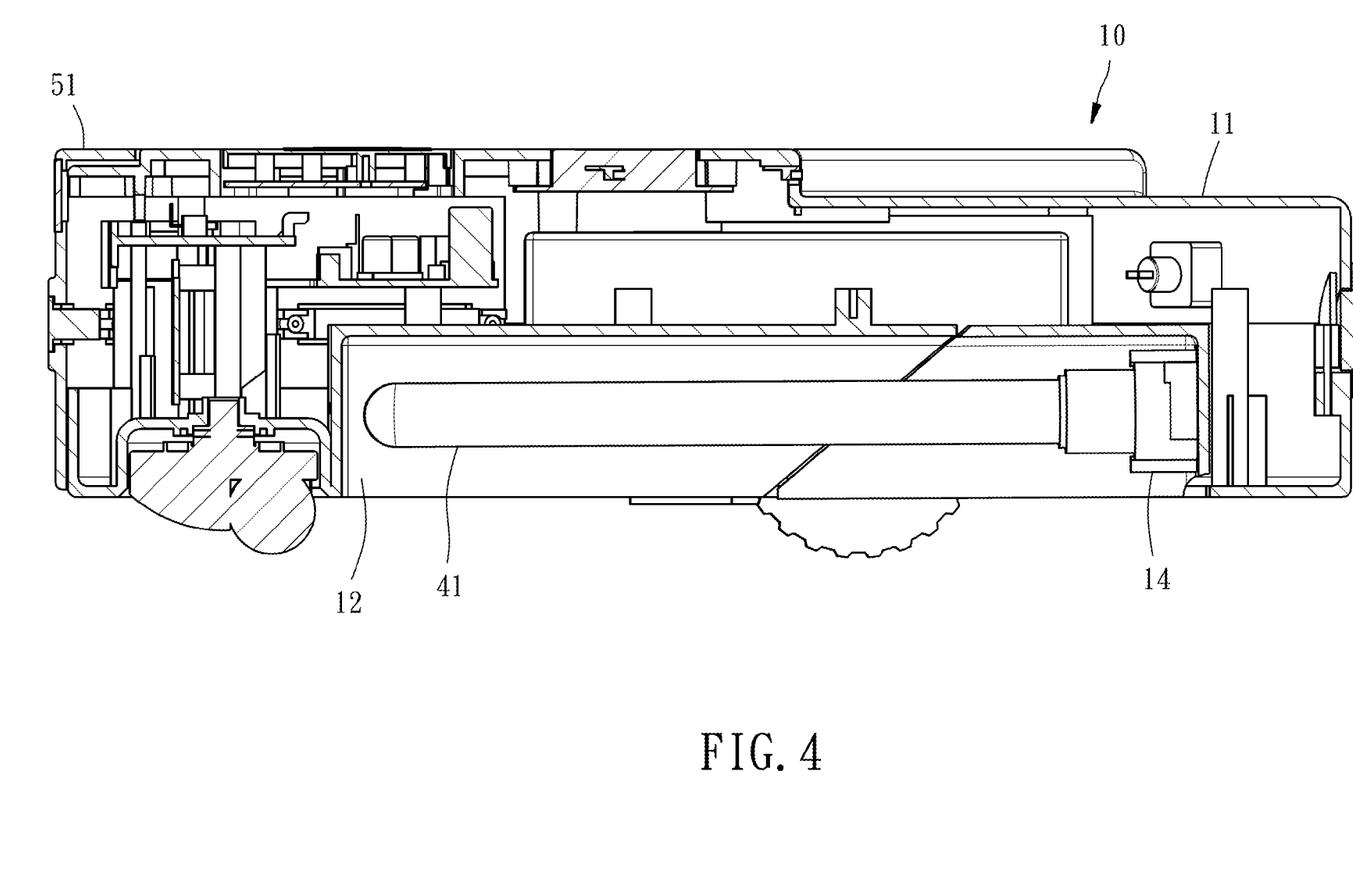
FIG. 4 is a sectional view taken along line 4-4 of FIG. 1.
Figure 5:
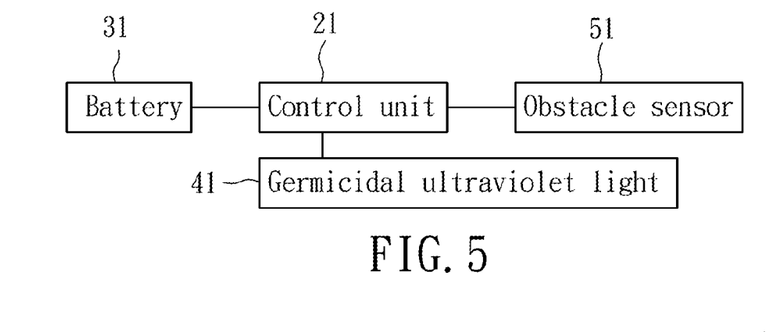
FIG. 5 is a circuit block diagram of the first embodiment of the present invention.
Figure 6:
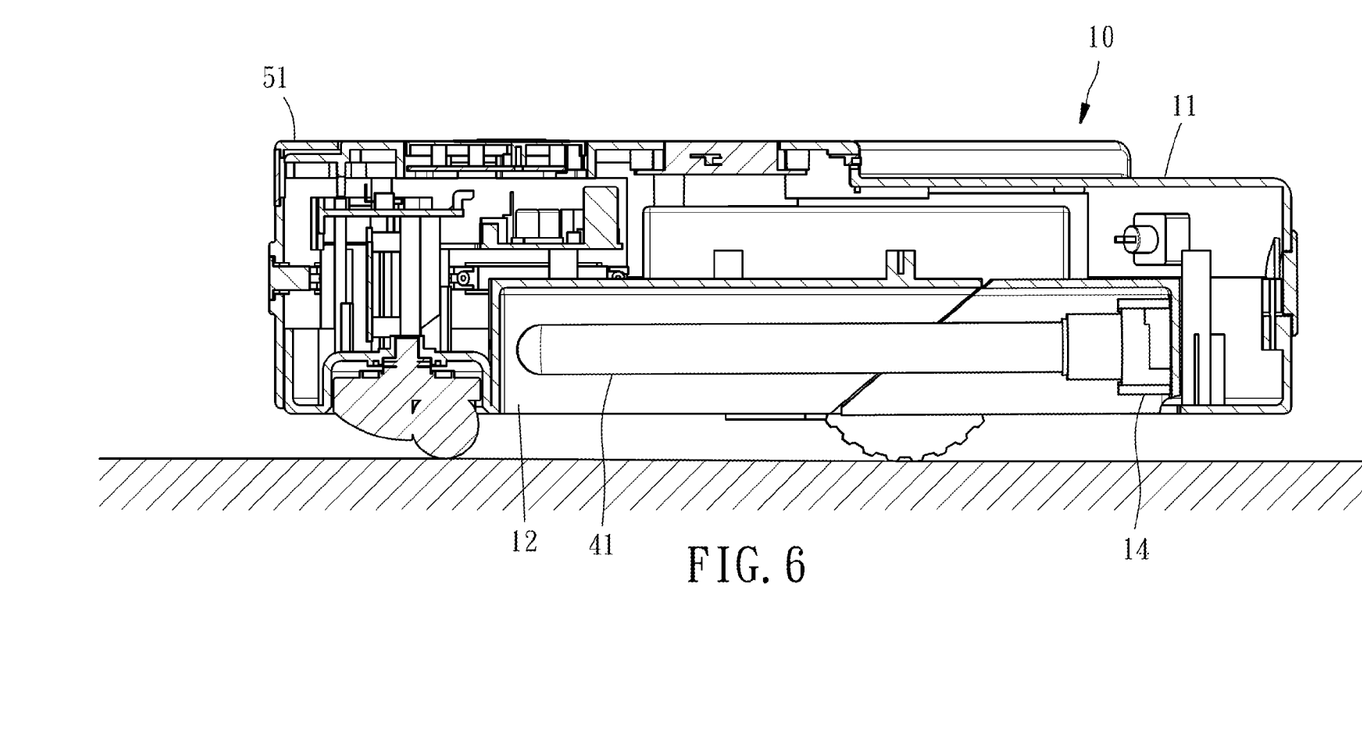
FIG. 6 is a schematic drawing illustrating an operational status of the self-propelled apparatus in accordance with the first embodiment of the present invention.

Referring to FIG. 6, in application, place the self-propelled apparatus 10 on the floor and turn it on. At this time, the control unit 21 turns on the two germicidal ultraviolet lights 41 and controls the self-propelled platform 11 to move in straight lines according to a predetermined grid-pattern. As the longitudinal axis of the germicidal ultraviolet light 41 exhibits a parallel relationship with the moving direction of the self-propelled platform 11 and the self-propelled platform 11 is mainly controlled to move in straight lines according to the predetermined grid-pattern, an intense UV dose can be applied by the germicidal ultraviolet lights 41 to the floor so as to achieve optimal bactericidal effects.

Figure 7:
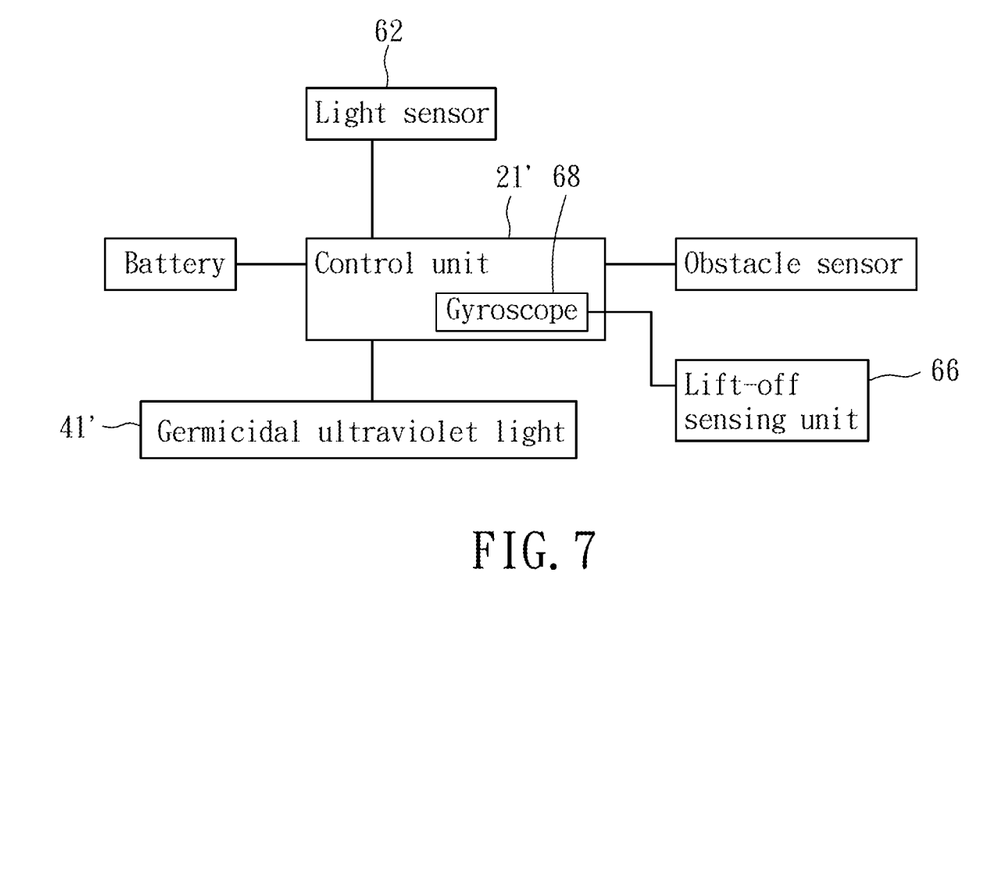
FIG. 7 is a circuit block diagram of a self-propelled apparatus in accordance with a second embodiment of the present invention.
Figure 8:
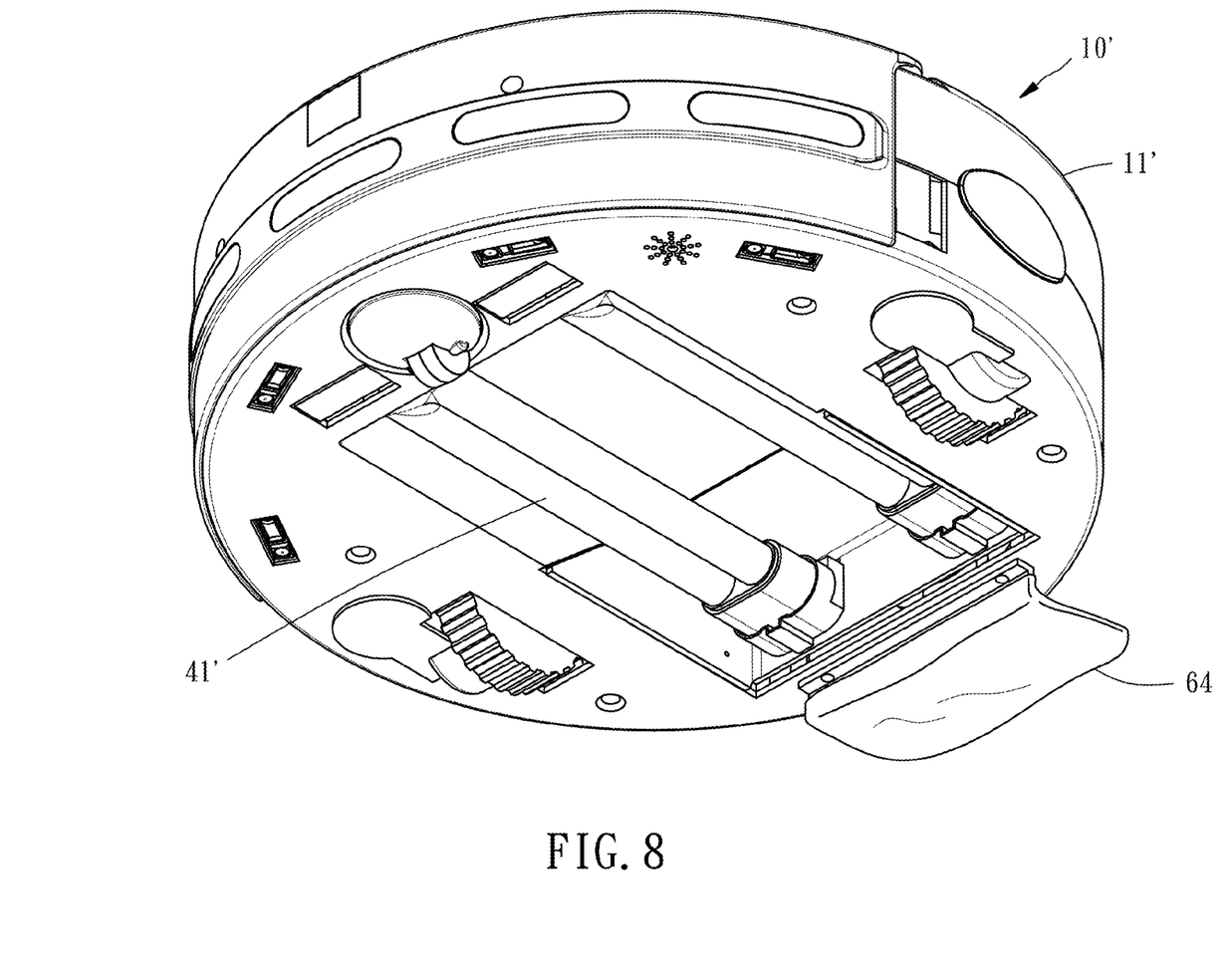
FIG. 8 is an oblique bottom elevational view of the self-propelled apparatus in accordance with the second embodiment of the present invention.

Referring to FIGS. 7 and 8, a self-propelled apparatus 10' having a bactericidal function in accordance with a second embodiment of the present invention is shown. This second embodiment is substantially similar to the aforesaid first embodiment with the exception as follows:

The self-propelled apparatus 10' of this second embodiment further comprises a light sensor 62, a micro-fiber pad 64 and a lift-off sensing unit 66; the control unit 21' further comprises a gyroscope 68.

The light sensor 62 is mounted in the self-propelled platform 11' and electrically coupled to the control unit 21', and adapted for sensing the light emitted by the germicidal ultraviolet lights 41'. Thus, by means of the sensing operation of the light sensor 62, the control unit 21' can check if the germicidal ultraviolet lights 41' work normally.

The micro-fiber pad 64 is mounted in the self-propelled platform 11'. When the self-propelled platform 11' is placed on the floor, the micro-fiber pad 64 is kept in contact with the floor, and thus, when self-propelled platform 11' is traveling, the micro-fiber pad 64 is move to wipe the floor. The micro-fiber pad is removable.

The lift-off sensing unit 66 is mounted in the self-propelled platform 11' and electrically coupled to the control unit 21', and adapted for detecting the moment the self-propelled platform 11' has been lift from the floor. Thus, if the self-propelled platform 11' is picked up from the floor or turns over, the control unit 21' immediately turns off the two germicidal ultraviolet lights 41', avoiding causing harm to the human eyes. In actual application, the lift-off sensing unit 66 can be a combination of a light emitter and a light receiver. The light emitter emits light toward the floor. The lift-off sensing unit receives reflected light from the floor for determining the distance from the floor. Alternatively, the lift-off sensing unit 66 can be a contact sensor that is kept in contact with the floor when the self-propelled platform 11' is placed on the floor, and the control unit 21' immediately judges that the self-propelled platform 11' is picked up from the floor or turns over if the contact sensor is not kept in contact with the floor. Or alternatively, the lift-off sensing unit 66 can be an accelerometer for detecting the dynamics of the self-propelled platform 11' so as to determine that the self-propelled platform 11' has left the floor.

The control unit 21' utilizes the gyroscope 68 to keep the self-propelled apparatus 10' moving in a straight line.

The other structural details of this second embodiment and the effects this second embodiment can achieve are same as the aforesaid first embodiment, no further detailed description in this regard will be necessary.

Figure 9:
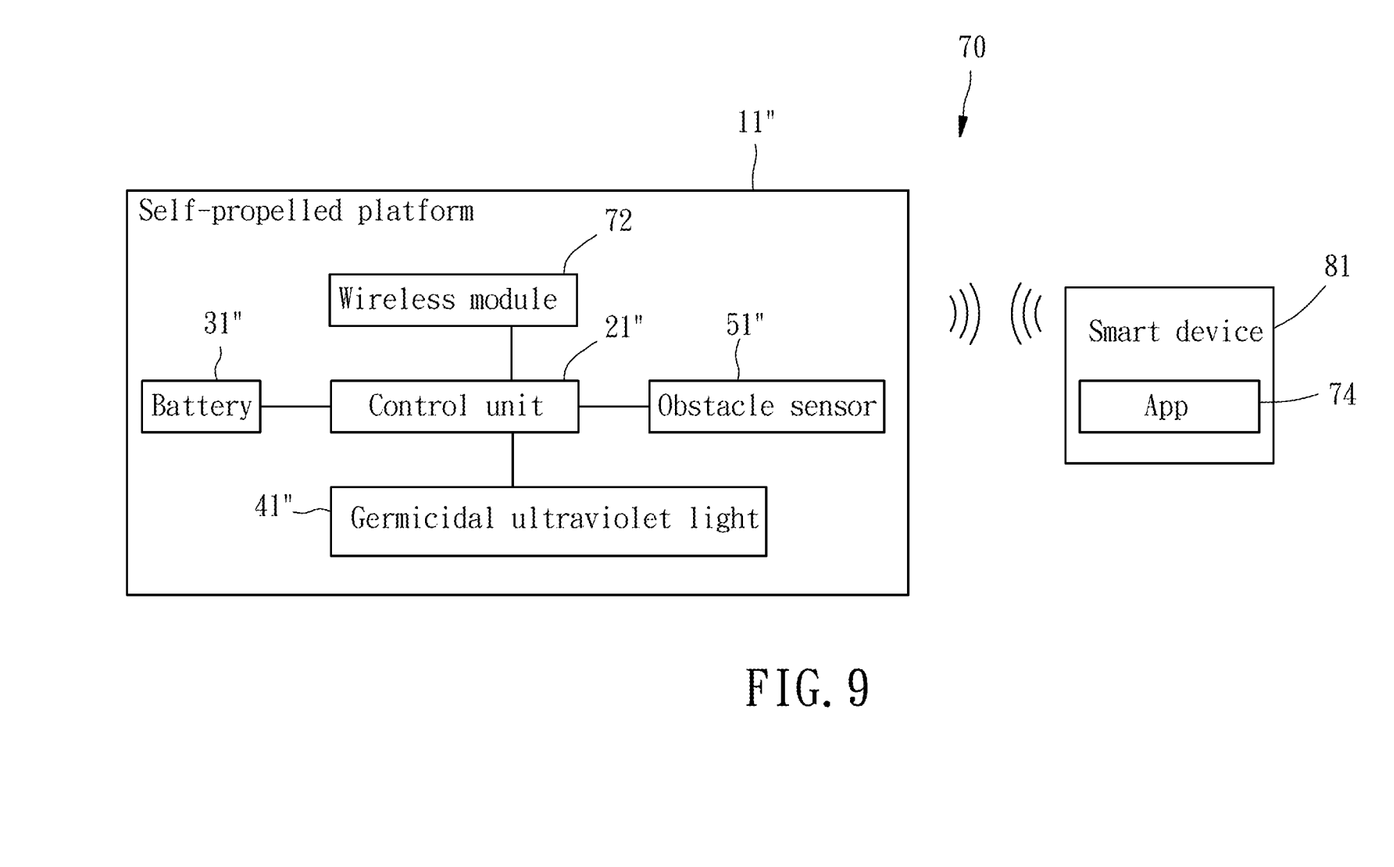
FIG. 9 is a circuit block diagram of a self-propelled apparatus in accordance with a third embodiment of the present invention.

Referring to FIG. 9, a self-propelled system having a bactericidal function in accordance with a third embodiment of the present invention is shown. The self-propelled system 70 comprises a self-propelled platform 11", a control unit 21", a battery 31", at least one germicidal ultraviolet light 41", and a plurality of obstacle sensors 51". These component parts are the same as that disclosed in the aforesaid first embodiment. The differences between this third embodiment and the aforesaid first embodiment are as follows:

The self-propelled system further comprises a wireless module 72 and application software (APP) 74.

The wireless module 72 is mounted in the self-propelled platform 11" and electrically coupled to the control unit 21" for wireless communication with a smart device (such as smart phone) 81.

The application software 74 is installed in the smart device 81 for execution by the smart device 81.

The self-propelled platform 11" utilizes the wireless module 72 to wirelessly communicate with the smart device 81 and transmitting data. The smart device 81 executes the application software 74 to interpret the data and displays the data in a way that a general user is able to understand, and also utilizes the wireless communication relationship between the smart device 81 and the wireless module 72 to transmit instructions to the control unit 21" for controlling the self-propelled platform 11". In the application, the data can contain path information, battery data, failure condition, and normal information of the operation of the germicidal ultraviolet light 41". When the smart device 81 executes the application software 74, it records the moving path of the self-propelled platform 11" according to the path information, and calculates the floor coverage of the moving path, enabling such information to be displayed in graphics or numeric values for the user's reference. Further, the smart device 81 can display the battery power level and the related operating conditions of the self-propelled platform 11" according to the content of the data. The wireless communication is optional and is not integral to the autonomous operation of the self-propelled platform.

The other structural details of this third embodiment and the effects this third embodiment can achieve are same as the aforesaid first embodiment, no further detailed description in this regard will be necessary.

Although particular embodiments of the invention have been described in detail for purposes of illustration, various modifications and enhancements may be made without departing from the spirit and scope of the invention. Accordingly, the invention is not to be limited except as by the appended claims.

What is claimed is:

1. A self-propelled apparatus, comprising:
   a self-propelled platform comprising a recessed chamber located in a bottom side thereof;
   a control unit mounted in said self-propelled platform, and adapted for controlling the moving path of said self-propelled platform in a predominantly grid-pattern that causes said self-propelled platform to mainly move in straight lines;
   a battery electrically coupled to said control unit to provide the necessary working electric energy;
   at least one germicidal ultraviolet light exhibiting an elongated shape and mounted in said self-propelled platform within said recessed chamber in such a manner that the longitudinal axis of said at least one germicidal ultraviolet light is kept in parallel to the linear moving direction of said self-propelled platform, said at least one germicidal ultraviolet light being electrically coupled to said control unit and controllable by said control unit to radiate light; and
   a plurality of obstacle sensors mounted in said self-propelled platform and electrically coupled to said control unit, and adapted for detecting the presence of obstacles for enabling said control unit to modify the traveling of said self-propelled platform on the basis of inputs from the said obstacle sensors.

2. The self-propelled apparatus as claimed in claim 1, wherein the depth of said recessed chamber is larger than the thickness of said at least one germicidal ultraviolet light, said at least one germicidal ultraviolet light being completely accommodated in said recessed chamber above the elevation of said bottom side of said self-propelled platform.

3. The self-propelled apparatus as claimed in claim 1, wherein the center of said at least one germicidal ultraviolet light is kept at a distance of approximately 2.5 cm above the floor when said self-propelled platform is placed on the floor.

4. The self-propelled apparatus as claimed in claim 1, wherein said self-propelled platform further comprises at least one lamp holder mounted in said recessed chamber; said germicidal ultraviolet light is detachably mounted in said at least one lamp holder.

5. The self-propelled apparatus as claimed in claim 1, further comprising a light sensor mounted in said self-propelled platform and electrically coupled to said control unit for detecting the ultraviolet light emitted by said at least one germicidal ultraviolet light.

6. The self-propelled apparatus as claimed in claim 1, wherein said control unit comprises a gyroscope.

7. The self-propelled apparatus as claimed in claim 1, wherein the number of said germicidal ultraviolet lights is 2, and the two said germicidal ultraviolet lights are arranged in parallel.

8. The self-propelled apparatus as claimed in claim 1, further comprising a micro-fiber pad mounted at said self-propelled platform, said micro-fiber pad being kept in contact with the floor when said self-propelled platform is placed on the floor.

9. The self-propelled apparatus as claimed in claim 1, further comprising a lift-off sensing unit mounted in said self-propelled platform and electrically coupled to said control unit for detecting if said self-propelled platform is picked up or turns over.

10. A self-propelled system, comprising:

a self-propelled platform comprising a recessed chamber located in a bottom side thereof;

a control unit mounted in said self-propelled platform, and adapted for controlling the moving path of said self-propelled platform in a predominantly grid-pattern that causes said self-propelled platform to mainly move in straight lines;

a battery electrically coupled to said control unit to provide the necessary working electric energy;

at least one germicidal ultraviolet light exhibiting an elongated shape and mounted in said self-propelled platform within said recessed chamber in such a manner that the longitudinal axis of said at least one germicidal ultraviolet light is kept in parallel to the linear moving direction of said self-propelled platform, said at least one germicidal ultraviolet light being electrically coupled to said control unit and controllable by said control unit to radiate light;

a plurality of obstacle sensors mounted in said self-propelled platform and electrically coupled to said control unit, and adapted for detecting the presence of obstacles for enabling said control unit to modify the traveling of said self-propelled platform from the inputs of said obstacle sensors;

a wireless module mounted in said self-propelled platform and electrically coupled to said control unit for communication with a smart device in a wireless manner; and an application software installed in said smart device for execution by said smart device;

wherein said self-propelled platform utilizes said wireless module to transmit data to said smart device; said smart device executes said application software to interpret said data and displays said data in a way that a general user is able to understand, and utilizes the wireless communication relationship between said smart device and said wireless module to transmit instructions to said control unit. This wireless communication is optional and not an integral component in the autonomous operation of the self-propelled platform.

11. The self-propelled system as claimed in claim 10, wherein said data contains a moving path data; said smart device records and displays the moving path of said self-propelled platform, and calculates the amount of floor coverage of said moving path when executing said application software.

12. The self-propelled system as claimed in claim 10, wherein the depth of said recessed chamber is larger than the thickness of said at least one germicidal ultraviolet light, said at least one germicidal ultraviolet light being completely accommodated in said recessed chamber above the elevation of said bottom side of said self-propelled platform.

13. The self-propelled system as claimed in claim 10, wherein the center of said at least one germicidal ultraviolet light is kept at a distance of approximately 2.5 cm above the floor when said self-propelled platform is placed on the floor.

14. The self-propelled system as claimed in claim 10, wherein said self-propelled platform further comprises at least one lamp holder mounted in said recessed chamber; said germicidal ultraviolet light is detachably mounted in said at least one lamp holder.

15. The self-propelled system as claimed in claim 10, further comprising a light sensor mounted in said self-propelled platform and electrically coupled to said control unit for detecting the ultraviolet light emitted by said at least one germicidal ultraviolet light.

16. The self-propelled system as claimed in claim 10, wherein said control unit comprises a gyroscope.

17. The self-propelled system as claimed in claim 10, wherein the number of said germicidal ultraviolet light is 2, and the two said germicidal ultraviolet lights are arranged in parallel.

18. The self-propelled system as claimed in claim 10, further comprising a micro-fiber pad mounted at said self-propelled platform, said micro-fiber pad being kept in contact with the floor when said self-propelled platform is placed on the floor.

19. The self-propelled system as claimed in claim 10, further comprising a lift-off sensing unit mounted in said self-propelled platform and electrically coupled to said control unit for detecting if said self-propelled platform is picked up or turns over.

* * * * *